United States Patent [19]
LaForge

[11] Patent Number: 5,012,176
[45] Date of Patent: Apr. 30, 1991

[54] APPARATUS AND METHOD FOR CALORIMETRICALLY DETERMINING BATTERY CHARGE STATE

[75] Inventor: David H. LaForge, Kensington, Calif.

[73] Assignee: Baxter International, Inc., Deerfield, Ill.

[21] Appl. No.: 503,837

[22] Filed: Apr. 3, 1990

[51] Int. Cl.$^5$ .................. G01N 27/46; H02J 7/00
[52] U.S. Cl. .................................. 320/31; 320/35; 320/43; 320/48; 324/427; 324/431
[58] Field of Search .................. 320/35, 36, 43, 14, 320/31, 48; 324/427, 431

[56] References Cited
U.S. PATENT DOCUMENTS

| | | | |
|---|---|---|---|
| 3,617,850 | 11/1971 | Domshy | 320/31 |
| 3,732,481 | 5/1973 | Mas | 320/14 |
| 4,151,454 | 4/1979 | Iida | 320/43 X |
| 4,153,867 | 5/1979 | Jungfer et al. | 320/43 |
| 4,423,378 | 12/1983 | Marino et al. | 320/48 X |

Primary Examiner—R. J. Hickey
Attorney, Agent, or Firm—McCubbrey, Bartels, Meyer & Ward

[57] ABSTRACT

The present invention is an apparatus and a method for determining the state of charge of a rechargeable battery. It comprises a means for charging the batter, current sensors, heat detectors for detecting the heat emanating from the battery during charging, with the heat being the complement of the charge acceptance percentage, and a processor for storing a mathematical charge acceptance model for providing the relationship between the charge acceptance percentage and the state of charge of the battery, and for calculating the state of charge of the battery from the heat detected by the heat detectors and the charge acceptance model. An accurate measure of battery charge state is produced while the battery is being charged. This provides information concerning the operability of the battery and also allows efficient charging to avoid energy waste. The present invention is adaptable to existing battery power systems without the need for significant additional components and is applicable to any system utilizing rechargeable batteries.

19 Claims, 3 Drawing Sheets

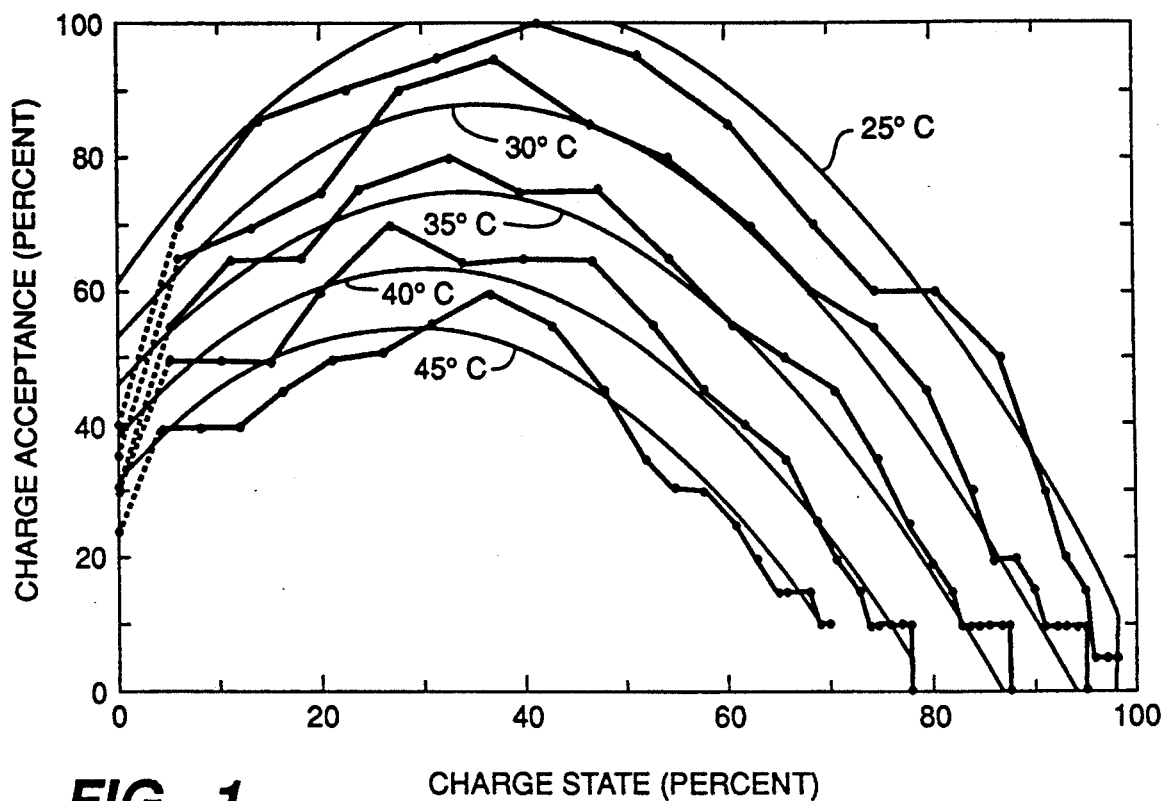
FIG. 1
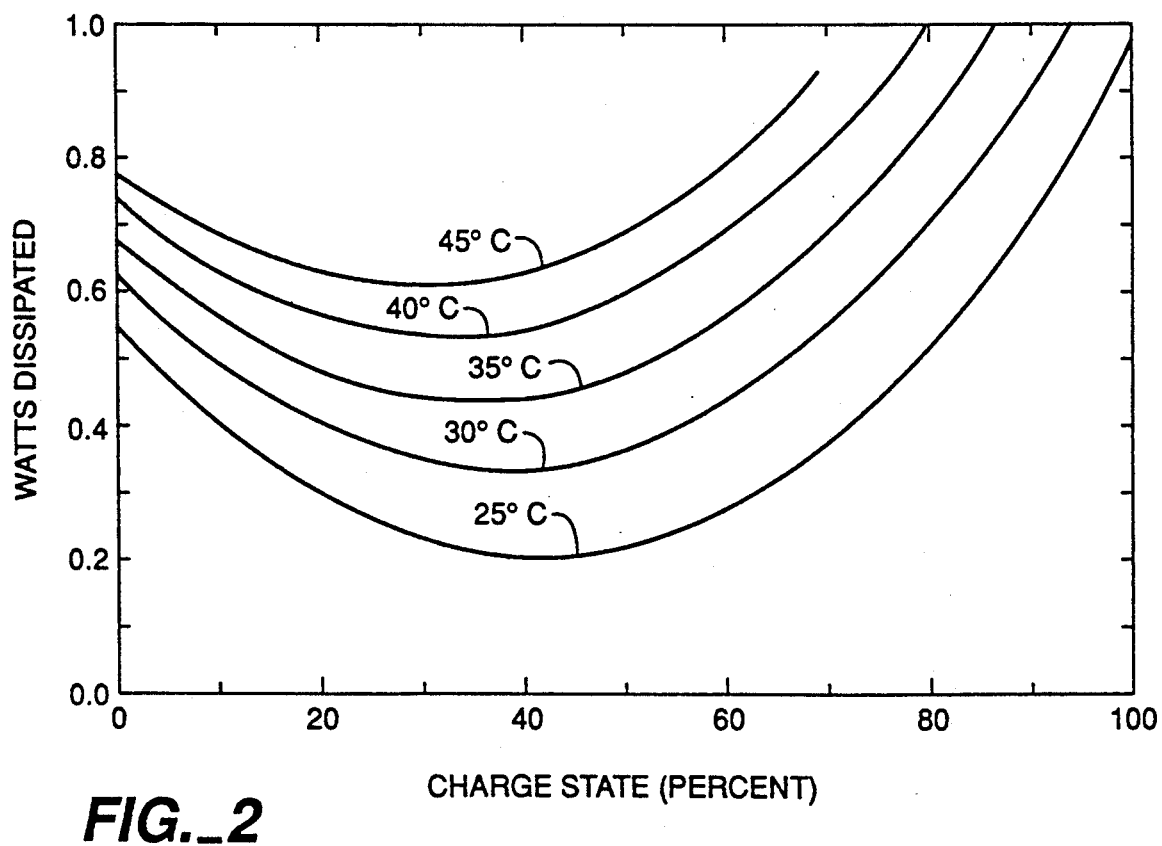
FIG._2

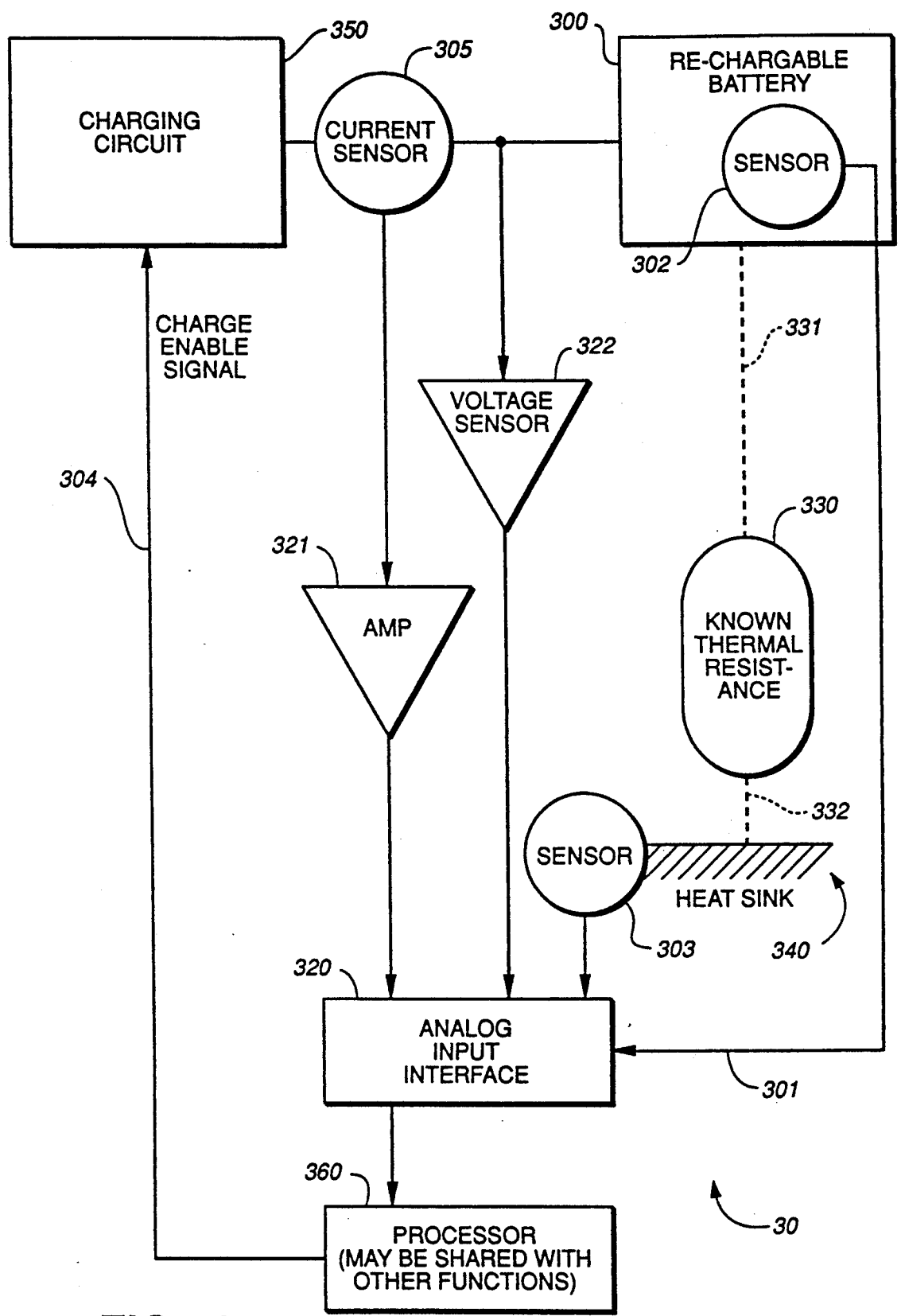
FIG._3

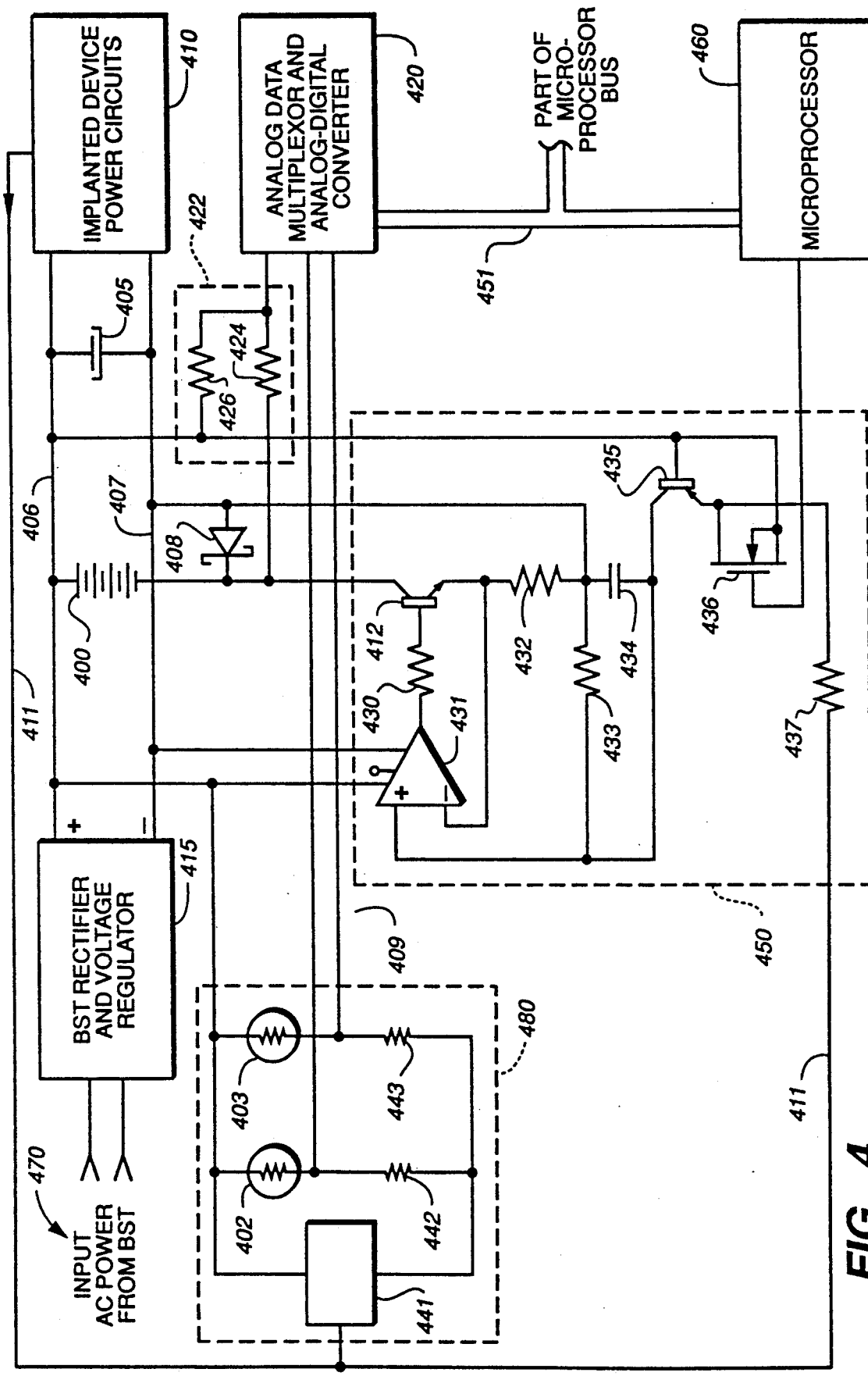
FIG._4

APPARATUS AND METHOD FOR CALORIMETRICALLY DETERMINING BATTERY CHARGE STATE

FIELD OF THE INVENTION

The present invention relates generally to the field of rechargeable batteries and more specifically to an apparatus and method for determining the state of charge of a rechargeable battery.

BACKGROUND OF THE INVENTION

Many devices in modern life require renewable energy sources for their operation. Among the more well-known of such devices are portable computers, electric vehicles, and medical prostheses. The importance of a reliable energy source for such devices is illustrated below taking medical prostheses as a specific example.

Many different kinds of medical prostheses have been implanted in hundreds of thousands of people every year. These devices can help to relieve pain, restore lost body functions, and even extend life itself. Examples of these devices are artificial hearts, pacemakers, hearing aids, drug delivery systems, nerve stimulators, and bone-growth stimulators.

It is highly desirable that these implanted devices be self-contained and self-sufficient to obviate the need for percutaneous energy transmission to the implanted device. A common method of providing energy to these devices is to use batteries.

A problem with batteries, however, is that they discharge to the point of inoperability after given periods of use. Thereafter, the batteries must either be replaced, or in the case of rechargeable batteries, recharged in order to continue operation of the device powered by the batteries.

"Storage" batteries can be recharged, with the state of charge being typically determined either roughly by a voltage test, which assumes that the battery output degrades steadily with time, or more precisely by a hygrometer which measures the specific gravity of the battery fluid which changes with use.

In many types of batteries, however, such methods of determining charge state are not possible. For example, the voltage output in nickel-cadmium (NiCd) batteries does not degrade steadily, but rather is substantially constant until complete discharge. Further, greater accuracy than that provided by a voltage test is often required. Since NiCd batteries are hermetically sealed, it is not possible or extremely inconvenient to measure the liquids (if any) in the battery.

Further, it is well known that a battery's capabilities change with variations in temperature, and the charge state of the battery must be determined taking the temperature environment into consideration.

One way of precisely determining the charge state is to allow the battery to run down to a zero charge state. This presents obvious problems of maintenance of the performance of the device being energized by the battery. This method clearly cannot be used in medical device applications as it presents a serious danger to patients. Solutions to the problem have included a signal warning to the patient requiring the patient to connect another energy source. This presents a problem for disabled or sleeping patients. Another solution is a monitoring computer which can be utilized to automatically connect another source of energy. This, however, presents other problems of device bulkiness and complexity as well as a need for a power source for the computer which itself may also run out.

As mentioned above, batteries such as the NiCd type, have a battery output that is substantially constant until just before running out, thereby giving little or no warning before complete discharge. In fact, batteries having such a characteristic output curve are desirable because gradual decreases of output indicate an increase in battery resistance which in turn indicates an inefficient battery which is not suitable for many purposes. Thus NiCd batteries offer the desirable characteristic of a stable output (which is necessary in many devices such as implanted prostheses), but that very stability makes it almost impossible to know the state of charge from a voltage output measurement.

One example of a prior art solution to these problems is U.S. Pat. No. 3,617,850 to Domshy which teaches a battery-status device utilizing the past history of the battery. If the amount of energy provided by a battery is recorded and the battery is recharged by pumping in a comparable amount of energy, a rough estimate is produced that the a battery is fully charged. It is only an estimate because as the battery ages and its operating temperature changes, the battery will not accept charge at the same efficiency and therefore is likely not in the fully charged state. Domshy alters the charge status indicator based on the charge/discharge history of the battery to compensate for the age of the battery and makes a temperature measurement to compensate for temperature changes.

Domshy's device has the disadvantage of requiring a number of sensors and recording devices in order to provide the necessary complete discharge/charge history of the battery. This may not be possible in many applications, particularly those of medical prostheses, and the additional components increase the complexity of the device.

Other prior art devices and methods require applying a predetermined load on the battery to determine status. An example of this kind of device, primarily useful for automobile batteries, is U.S. Pat. No. 4,423,378 to Marino et al.

In electronic medical prosthetic devices, the battery in the device is typically in a body-implant system where applying loads and making external measurements is extremely difficult if not impossible.

Finally, in order to efficiently charge a battery the state of charge should be known so that time and energy are not wasted in continuing to charge a battery which has already reached its charge acceptance limit.

Thus there is a distinct need for knowledge of the state of charge of a battery which can be determined without the necessity of intrusive procedures or added device complexity requiring continual monitoring and recording.

SUMMARY OF THE INVENTION

The present invention is an apparatus and a method for determining the state of charge of a rechargeable battery. Broadly, it comprises a means for charging the battery, a current sensor for sensing the current entering the battery, heat detectors for detecting the heat emanating from the battery during charging, with the heat being the complement of the charge acceptance percentage, and a processor for storing a mathematical charge acceptance model for providing the relationship between the charge acceptance percentage and the state of charge of the battery, and for calculating the state of charge of the battery from the heat detected by the heat detectors and the charge acceptance model.

The present invention provides an accurate measure of battery charge state while the battery is being charged. Knowledge of the charge state not only provides information concerning the operability of the battery, but also allows efficient charging since the state of maximum charge will be known and the charging process can be terminated to avoid energy waste. In many applications, there are no additional intrusive devices or methods required, producing the advantages of reduced weight, size, and complexity. The present invention is adaptable to existing battery power systems without the need for significant additional components and is applicable to any system utilizing rechargeable batteries.

A further understanding of the nature and advantages of the present invention may be realized by reference to the remaining portions of this application and the attached drawings.

BRIEF DESCRIPTION OF THE DRAWINGS

FIG. 1 illustrates a mathematical model based on empirical data representing the relationship between the percentage of charge acceptance by a battery and the percentage charge state of the battery with temperature as a parameter according to one embodiment of the present invention.

FIG. 2 illustrates the relationship between the percentage of heat dissipated by a battery and the percentage charge state of the battery with temperature as a parameter according to one embodiment of the present invention.

FIG. 3 is a block diagram schematically illustrating the charge state determination apparatus according to the present invention.

FIG. 4 is a schematic diagram of one embodiment of one application of the apparatus to determine charge state while charging a battery according to the present invention.

DETAILED DESCRIPTION OF THE INVENTION

The present invention utilizes a mathematical model based on empirical data representing the relationship between the percentage of charge acceptance by a battery during charging and the percentage charge state of the battery with temperature as a parameter.

Batteries can be characterized by charge and discharge rates relative to a one hour rate, termed a "C rate". That is, if the battery is charged or discharged in one hour, it is "C", if the battery is charged or discharged over 10 hours, the rate is "C/10". This is a nominal charge rating, so for an older battery which will not take that much charge, it does not affect the current that is equivalent to charging at C/10. For example, if a NiCd cell is rated at 1300 milli-ampere-hours (mAH), the C/10 rate is 130 mA.

NiCd batteries are constructed such that the gases produced can be recombined by overcharging at the C/10 rate. As the battery will accept all the charge up to a limit, thereafter, the energy goes into electrolysis and the electrolyte generates hydrogen and oxygen and they recombine by virtue of the design structures of the battery. Therefore, the battery can tolerate C/10 charging rates over extended periods and avoid developing a destructive gas pressure. Thus the relatively slow C/10 charge rate can be an intrinsically safe charge rate which does not require active intervention to contend with the gas pressure and maintain safety. Faster charging rates may require intervention which, in many cases such as medically required body implants, is often extremely difficult and dangerous.

The advantage of a higher charge rate is to charge a battery more rapidly. However, the competing reactions of decomposition of the electrolyte and recombination become more significant as full charge is approached.

An example of a charge acceptance model for a C/10 charge rate is shown in FIG. 1 with charge acceptance percentage as the ordinate and percentage charge state as the abscissa. The squares are data points with connecting lines and the curves are least-squares fits of the data. It can be seen that, as temperature increases, the charge acceptance percentages decrease markedly. For example, at a temperature of 40° C., a battery which has a charge state of 80% will no longer accept any further charge at this C/10 rate.

It is known in the art that different charging rates may produce better charge acceptance. If the rate of charge is C/3, the family of curves as in FIG. 1 would be pushed upwards providing better charge acceptance percentages by forcing more charge into the battery. However, a higher charge rate may generate unacceptable levels of heat and gas pressure rendering the battery unsafe and thereby requiring constant monitoring and intervention. If the gases are vented, the lost gases will degrade the battery performance and lifetime and present serious problems in the immediate environment. These difficulties can be overcome by charging intermittently, but this will increase the time required for charging. It is understood that any charge rate producing a charge acceptance model is within the scope of the present invention and that the choice depends on the trade-off between reduced charge acceptance and increased safety and reduced maintenance requirements and possibly the time required for intermittent charging.

During charging of a battery, based on the data in FIG. 1 alone, it is not possible to accurately determine position on the curves and therefore the charge state of the battery cannot be known with acceptable accuracy. Further, as can be seen from the curves at greater than about 40% charge state, for this type of battery the curves fall off gradually so the end of charge of the battery is not signaled to the user.

Broadly stated, the present invention recognizes that the amount of energy not entering the battery is dissipated into heat and is just the complement to the charge acceptance percentage shown in FIG. 1. That is, (1—charge acceptance) is the dissipated heat which is shown in FIG. 2 as a function of charge state. The charge state must first be roughly determined to be greater than about 40% so as to be on the right side of FIG. 2. This can be done in several ways, for example, by noting that the heat measured is increasing or by doing a standard voltage test. Then by measuring the heat evolved by the battery as the battery is charged, the charge state can be determined as illustrated in FIG. 2. Since a fixed amount of power is input at a fixed rate, and the temperature is measured, then the particular curve and the position on that curve can be determined and the state of charge is known from the abscissa.

As an example of one such calculation for the family of curves of FIG. 1, the incremental charge acceptance (dg/dx) for this example can be adequately represented mathematically by a family of parabolae with characteristics determined by the temperature:

$$dg/dx = kb/2 - KQ^2/2b \qquad (1)$$

where q is the charge state ($0 \leq q \leq 1$); x is the charge input relative to q ($x \geq q$); Q is the charge state q centered on $(dg/dx)_{max}$; and k and b are coefficients which depend on temperature only.

From the charge acceptance model of FIG. 1, a function (dependent on temperature) representing incremental charge state as a function of incremental charge input (dg/dx) can be empirically defined as:

$$f(T) = \exp(c - aT) \qquad (2)$$

where T is in °C. The function f(T) is approximately unity for T=25° C. and below (as can be seen in FIG. 1 for the lower right hand side charge acceptance curve for T=25° C.). This represents the final charge state obtainable at the C/10 charge rate. The maximum charge acceptance, which is the peak of the T=25° C. curve (showing 100% charge acceptance), can be represented by f(T) squared. That is, the dependence of the maxima of the family of curves in FIG. 1 as a function of temperature is $f^2$. Thus, $f^2$ gives the incremental charge acceptance at its peak. In other words, a function f is defined which gives a unity value at the final charge state and has a squared value at the charge acceptance peak. The family of curves of FIG. 1 intersect the ordinate at the initial charge acceptance which is represented by h. For example, at T=25° C., h is approximately 0.5.

Given the boundary and initial conditions constraining f above, a general equation describing the charge state q as a function of the charge input x, can be derived using, for example, a least-squares regression calculation. In addition, since it is the charge state as a function of charge input that is of interest, the variable Q (as in Equation (1) must be changed to x.

The temperature-dependent coefficients can then be derived as:

$$k = 2f(1 + \sqrt{(1-h)}) \qquad (3)$$

$$b = 2f^2/k = (f/h)(1 - \sqrt{(1-h)}) \qquad (4)$$

$$Q = q - b\sqrt{(1-h)} = q - f + b \qquad (5)$$

Since k and b are functions of f and h only, only three arbitrary constants (h, a, and c) are needed to produce q(x,T). Changing the independent variable from Q to x and integrating Equation (1) results in the parabolic curves being integrated to give a ratio of exponentials (rather than a cubic) as follows:

$$q = b \frac{(e^{kx} - c)}{(e^{kx} + c)} + f - b \qquad (6)$$

where $c = f/(2b - f)$. It is understood that the values of the arbitrary constants and temperature coefficients depend on the characteristics of the curves representing the charge acceptance as a function of charge state and that other choices of curves (such as hyperbolic curves) may in some cases better fit the empirical data. Also, the charge rate in the exemplary embodiment was C/10, it is further understood that different charge rates will produce different types of temperature-dependent curves and that all such curves, as long as they represent a charge acceptance as a function of charge state, are within the scope of the present invention.

From measurements of temperature T and input charge x, and representations of the curves giving the constants c and b, the state of charge q may be calculated. Various methods of mathematically representing the curves may be employed, with the example given as a least-squares fit method of regression analysis.

The preferred embodiment of the apparatus of the present invention is broadly shown in block diagram form in FIG. 3. An apparatus 30 charges a rechargeable battery 300 having a temperature sensor 302 for sensing the temperature of battery 300. This temperature is communicated to an analog input interface device 320 through line 301. A heat sink 340 represents anything external to battery 300, for example the outer surface of a device utilizing battery 300. Heat sink 340 also includes a temperature sensor 303 which is also coupled to analog input interface device 320. Any material 330 having a known thermal resistance is disposed between battery 300 and heat sink 340. For example, thermal resistance 330 could be the materials between the battery and the outer surface of the casing of the device utilizing the battery. The dashed lines 331 and 332 represent heat flux. A charging circuit 350 is coupled to battery 300 via an optional current sensor 305 which is coupled via an amplifier 321 to analog input interface device 320. The current input into battery 300 is also fed through a voltage sensor 322 to analog input interface device 320. A processor 360 is coupled to analog input interface device 320 and to charging circuit 350 through line 304. Processor 360 contains the charge acceptance mathematical model given by Equation (6) and receives inputs from analog input interface device 320.

In operation, battery 300 begins charging upon receipt by charging circuit 350 of a charge enable signal from processor 360. While charging, a measurement of the energy flowing into the battery is made utilizing current sensor 305 and voltage sensor 322 to determine the voltage under varying conditions of temperature and state of charge. This gives x, the input charge, in Equation (6). The temperature values provided to processor 360 produce the function f and the temperature dependent coefficients, and processor 360 calculates the charge state q, which may be displayed. Processor 360 also can stop charging circuit 350 from charging battery 300 when the maximum charge state for a given temperature is achieved, thereby rendering the charging process efficient and non-wasteful.

To operate properly, the charge state must be on the greater than 40% charge state side of the curves of FIG. 2. This can be determined by a voltage test or by monitoring the heat dissipated such that when heat dissipation begins increasing, the charge state position is on the right hand side of the curves of FIG. 2.

In the preferred embodiment, a pack holding battery 300 is made isothermal so as to obtain accurate heat dissipation measurements free from influences other than battery heat dissipation. Specifically, all cells in battery 300 are held to the same temperature so that the same curve of the family of curves of FIG. 1 will hold for all cells.

A more detailed description of a particular embodiment of the present invention is given in FIG. 4 as an example of an application of the present invention.

Other applications will be apparent to those skilled in the art. The specific components employed are exemplary with the understanding that other components may be substituted therefor in a manner known in the electronic arts.

FIG. 4 illustrates an implanted prosthetic device having power circuits 410 and powered inductively by AC power from a belt skin transfer (BST) device 470 via a rectifier and voltage regulator 415, a battery 400 and a DC filter capacitor 405. Battery 400 (for example, eight NiCd cells in series) provides direct current power to the power circuits 410 of the prosthetic device in parallel with BST device 470 via lines 406 and 407. The negative terminal of battery 400 is coupled to a battery-run diode 408 which is coupled to line 407 and a charging control circuit 450.

Charging control circuit 450 comprises a transistor 412 having an emitter coupled to the negative terminal of battery 400 and diode 408. An amplifier 431 is coupled through a resistor 430 to the base of transistor 412 and has an inverting input coupled to the collector of transistor 412 and a resistor 432. The non-inverting input of amplifier 431 is coupled to a resistor 433 which in turn is coupled to resistor 432 and a filtering capacitor 434 which is itself coupled to the collector of transistor 435. Transistor 435 has a base coupled to line 406 and to voltage divider 422 (comprising resistors 423 and 424) which itself is coupled to an analog data multiplexer and analog-to-digital converter (ADC) 420. The emitter of transistor 435 is coupled to a switch transistor 436 which itself is coupled to the base of transistor 435 and line 411 through a resistor 437. Switch 436 is also coupled to a microprocessor 460.

A temperature sensing circuit 480 comprises a thermistor 402, disposed in battery 400, a thermistor 403 disposed on the battery case, a voltage regulator 441 coupling thermistors 402 and 403 and ballast resistors 442 and 443. Temperature sensor 480 is coupled to analog data multiplexer and ADC 420 via line 409. Analog data multiplexer and ADC 420 is coupled to microprocessor 460 via bus 451.

In typical operation, BST device 470 provides AC power which, after rectification, provides a higher DC voltage than does battery 400 and thus provides DC power to power circuits 410 and charges battery 400 at the same time. Diode 408 causes battery power to be applied to power circuits 410 whenever inductive power from BST device 470 is absent. Charging control circuit 450 causes battery 400 to be charged responsive to control signals from microprocessor 460 through switch 436. Temperatures are monitored by temperature sensor 480 by means of thermistors 402 and 403, which have temperature readings rendered linear by ballast resistors 442 and 443, and which communicate temperature values to analog data multiplexer and ADC 420 which in turn transmits digitized data to microprocessor 460 for computation of charge state in conjunction with the aforesaid mathematical model of charge acceptance. Voltage test readings of battery 400 (for roughly determining position on the charge acceptance curves of FIG. 2), are made through voltage divider 422.

The embodiment of FIG. 4 describes an inductive charging of battery 400 by a BST-type device 470. It is understood that any power source, AC or DC, could be used to charge battery 400 and/or provide power to power circuits 410. For example, a set of percutaneous terminals could be utilized for hook-up with any type of power source.

In the preferred embodiment of the present invention, the computations are done digitally. It is within the scope of the present invention to perform the calculations in an analog manner. That is, a circuit may be designed to perform the measurements and calculations described, the functions of required components being known in the art. For example, a capacitor can be utilized to serve as a memory for the immediate state-of-charge history.

Although the above description was made with reference to a specific example of medical application, it is understood that the present invention is applicable to any device utilizing a rechargeable energy source and is capable of determining the state of charge of any rechargeable battery where charge acceptance is a function of both state of charge and temperature as exemplified in FIG. 1. The present invention is particularly valuable for devices operating at, or in an environment of, elevated temperatures.

While the above description provides a full and complete description of the preferred embodiments of the present invention, various modifications, alternate constructions and equivalents may be employed. Therefore, the above description and illustrations should not be construed as limiting the scope of the invention which is defined by the following claims.

I claim:

1. An apparatus for determining the state of charge of a rechargeable battery comprising:
   charging means, coupled to the battery, for charging the battery;
   current sensing means, coupled between said charging means and the battery, for sensing the current entering the battery;
   heat detecting means, coupled to the battery, for detecting the heat emanating from the battery during charging; and
   processing means, coupled to said current sensing means and to said heat detecting means, including a mathematical charge acceptance model providing the relationship between a charge acceptance percentage and the state of charge of the battery, for calculating the state of charge of the battery from the current entering the battery the heated detected by said heat detecting means, and said charge acceptance model, wherein said heat is the complement of said charge acceptance percentage.

2. The apparatus of claim 1 wherein said heat detecting means further comprises a temperature sensing means and said charge acceptance model includes temperature of the battery as a parameter.

3. The apparatus of claim 1 wherein said charge acceptance model comprises at least one parabolic representation of the charge acceptance percentage as a function of the charge state percentage, each of said parabolae having a temperature parameter.

4. The apparatus of claim 1 wherein said charge acceptance model includes curve-fitting means for fitting empirical data and for providing mathematical representations thereof.

5. The apparatus of claim 1 further comprising a voltage sensing means, coupled to the battery, for sensing the voltage of the battery.

6. The apparatus of claim 1 wherein the battery is encased by an isothermal casing.

7. The apparatus of claim 6 wherein said heat detecting means includes at least one first thermistor disposed on the battery and at least one second thermistor disposed on said casing, and a predetermined thermal resistance between the battery and said casing.

8. The apparatus of claim 1 wherein said processing means includes an analog data multiplexer, an analog-to-digital converter, and a microprocessor.

9. The apparatus of claim 1 wherein said charging means further comprises a switch means coupled to said processing means turning on and off said charging means.

10. The apparatus of claim 1 wherein said charging means comprises an inductive AC power source, coupled to a rectifier and voltage regulator in parallel with the battery, and a battery-controlled diode for charging the battery and for providing an alternate energy source to the battery.

11. A method for determining the state of charge of a rechargeable battery comprising:
mathematically modeling the relationship between the charge acceptance percentage and the state of charge of the battery;
charging the battery;
detecting the current entering the battery;
detecting the heat emanating from the battery during charging, said heat flux being the complement of the charge acceptance percentage; and
storing said charge acceptance model in a processor and calculating the state of charge of the battery from the current entering the battery, the heat detected and said charge acceptance model.

12. The method of claim 11 wherein said charge acceptance model includes temperature of the battery as a parameter.

13. The method of claim 11 wherein said charge acceptance model utilizes at least one parabolic representation of the charge acceptance percentage as a function of the charge state percentage, each of said parabolae having a temperature parameter.

14. The method of claim 11 wherein said step of mathematically modeling the charge acceptance includes curve-fitting empirical data for providing mathematical representations thereof.

15. The method of claim 11 further including the step of sensing the voltage of the battery.

16. The method of claim 11 further including the step of isothermally encasing the battery.

17. The method of claim 16 wherein said heat detecting step includes sensing the temperature of the battery and the encasement of the battery, and disposing a predetermined thermal resistance between the battery and the encasement.

18. The method of claim 11 further including the step of transmitting a signal from said processor to stop said charging of the battery upon achieving a predetermined state of charge of the battery.

19. The method of claim 11 further including the step of charging the battery utilizing an inductive AC power source, rectifying and regulating the AC power, and providing an alternate energy source to the battery utilizing said inductive AC power source.

* * * * *